(12) United States Patent
Guan et al.

(10) Patent No.: US 9,557,957 B2
(45) Date of Patent: Jan. 31, 2017

(54) SYSTEM AND METHOD FOR DEVELOPING A MODEL INDICATIVE OF A SUBJECT'S EMOTIONAL STATE WHEN LISTENING TO MUSICAL PIECES

(71) Applicant: Agency for Science, Technology, and Research, Singapore (SG)

(72) Inventors: Cuntai Guan, Singapore (SG); Juanhong Yu, Singapore (SG); Yaozhang Pan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/428,852

(22) PCT Filed: Sep. 17, 2013

(86) PCT No.: PCT/SG2013/000404
§ 371 (c)(1),
(2) Date: Mar. 17, 2015

(87) PCT Pub. No.: WO2014/042599
PCT Pub. Date: Mar. 20, 2014

(65) Prior Publication Data
US 2015/0235134 A1    Aug. 20, 2015

(30) Foreign Application Priority Data
Sep. 17, 2012   (SG) ............... 201206897-9

(51) Int. Cl.
*G06F 17/00* (2006.01)
*G06F 3/16* (2006.01)
(Continued)

(52) U.S. Cl.
CPC ............ *G06F 3/165* (2013.01); *A61B 5/0476* (2013.01); *A61B 5/04845* (2013.01); *A61M 2230/10* (2013.01)

(58) Field of Classification Search
CPC ............... A61M 2230/10; A61M 2021/0027; A61B 5/04008; A61B 5/0476; G10H 2220/376; G06F 3/165
See application file for complete search history.

(56) References Cited

U.S. PATENT DOCUMENTS 4,883,067 A * 11/1989 Knispel ............... A61B 5/0482 600/28
5,667,470 A * 9/1997 Janata ................. A61M 21/00 600/28

(Continued)

FOREIGN PATENT DOCUMENTS

WO   WO-2014/042599   3/2014

OTHER PUBLICATIONS

"International Application No. PCT/SG2013/000404, International Search Report and Written Opinion mailed Oct. 31, 2013", (Oct. 31, 2013), 8 pgs.

(Continued)

*Primary Examiner* — Andrew C Flanders
(74) *Attorney, Agent, or Firm* — Schwegman Lundberg & Woessner, P.A.

(57) ABSTRACT

A method for deriving optimal discriminating features indicative of a subject state when the subject listens to one of a set of musical pieces, comprising a step of extracting frequency features from the subject's EEG signal when the subject is in a first subject state and a second subject state, the frequency features being extracted from more than one frequency band in one set of time segments; and identifying optimal discriminating features from the extracted frequency features, the optimal discriminating features indicative of characteristics of the EEG signal when the subject is in the first subject state and the second subject state, wherein one of the first subject state and the second subject state (Continued)

indicates that the subject likes a musical piece while the other state indicates that the subject does not like the musical piece.

18 Claims, 7 Drawing Sheets

(51) Int. Cl.
*A61B 5/0484* (2006.01)
*A61B 5/0476* (2006.01)

(56) References Cited

U.S. PATENT DOCUMENTS

2006/0251303 A1* 11/2006 He .................. A61B 5/04008
382/128
2010/0056854 A1* 3/2010 Chang ................ A61M 21/00
600/28

OTHER PUBLICATIONS

Schmidt, Louis A., et al., "Frontal brain electrical activity (EEG) distinguishes valence and intensity of musical emotions", Cognition and Emotion, 2001, 15 (4), 487-500, (Jul. 1, 2001), 487-500.

* cited by examiner

SYSTEM AND METHOD FOR DEVELOPING A MODEL INDICATIVE OF A SUBJECT'S EMOTIONAL STATE WHEN LISTENING TO MUSICAL PIECES

PRIORITY CLAIM TO RELATED APPLICATIONS

This application is a U.S. National stage application filed under 35 U.S.C. §371 from International Application Serial No. PCT/SG2013/000404, which was filed Sep. 17, 2013, and published as WO 2014/042599 on Mar. 20, 2014, and which claims priority to Singapore Application No. 201206897-9 filed Sep. 17, 2012, which applications and publication are incorporated by reference as if reproduced herein and made a part hereof in their entirety, and the benefit of priority of each of which is claimed herein.

FIELD OF INVENTION

The invention relates generally to brain computer interface, and more particularly to musical scoring in response to a subject's measured emotional state.

BACKGROUND

People usually identify features of a musical piece so as to categorize similar musical pieces together. In most cases, the categorization is done manually according to a subject's preference. It is known that music has several positive effects on a subject and listening to preferred music will have a greater positive effect on the subject.

One conventional technique is to identify genres or musical characteristics as the features of the musical pieces. It may in many instances result in inaccurate categorization of musical pieces, since there are only limited genres (e.g. jazz and rock) and musical characteristics (e.g. pitch and tempo). Further, a musical song that has a positive effect on a person may not have the same effect on another person.

Thus, it would be beneficial to categorize musical pieces automatically in response to the effect on the subject. However, with the existing techniques and tools, it is difficult to provide a method that effectively categorizes musical pieces to cause a positive effect on a subject.

A need therefore exists to provide a system and method which can be used to automatically derive features that are indicative of a subject state when the subject listens to a musical piece.

SUMMARY

According to a first aspect, there is provided a method for deriving optimal discriminating features indicative of a subject state when the subject listens to one of a set of musical pieces, comprising: extracting frequency features from the subject's EEG signal when the subject is in a first subject state and a second subject state, the frequency features being extracted from more than one frequency band in one set of time segments; and identifying optimal discriminating features from the extracted frequency features, the optimal discriminating features indicative of characteristics of the EEG signal when the subject is in the first subject state and the second subject state, wherein one of the first subject state and the second subject state indicates that the subject likes a musical piece while the other state indicates that the subject does not like the musical piece.

According to a second aspect of the invention, there is provided a method for developing a model indicative of a subject state when the subject listens to one of a set of musical pieces, comprising extracting frequency features from the subject's EEG signal when the subject is in a first subject state and a second subject state, the frequency features being extracted from more than one frequency band in one set of time frames; identifying optimal discriminating features from the extracted frequency features, the optimal discriminating features indicative of similar characteristics of the EEG signal when subject is in the first subject state and the second subject state; extracting musical features associated with each of a set of the musical pieces; comparing the extracted musical features with the optimal discriminating features to determine which of the extracted musical features are indicative of characteristics of musical pieces that the subject prefers; and developing a model in response to the optimal discriminating features of the subject when listening to one of the set of the musical pieces and the musical features for the one of the set of the musical pieces, wherein one of the first subject state and the second subject state indicates that the subject likes a musical piece while the other state indicates that the subject does not like the musical piece.

According to a third aspect of the invention, there is provided a system for developing a model indicative of a subject state when the subject listens to one of a set of musical pieces, comprising: an input device for the system operable to receive electroencephalography (EEG) signal; an EEG discriminative feature generator operable to extract frequency features from the received EEG signal when the subject is in a first subject state and a second subject state and identify optimal discriminating features from the extracted frequency features, the optimal discriminating features indicative of similar characteristics of the EEG signal when subject is in the first subject state and the second subject state; a model builder operable to develop a model in response to the optimal discriminating features of the subject when listening to one of the set of the musical pieces and the musical features for the one of the set of the musical pieces; a music scorer operable to generate a musical preference score for each of the set of the musical pieces, the musical preference score indicating the subject's preference of the musical piece; and a music controller operable to control the set of the musical pieces, wherein the musical pieces is controlled to stop playing when the musical preference score indicates that the subject does not like the musical piece, and to continue when the musical preference score indicates that the subject does like the musical piece, wherein one of the first subject state and the second subject state indicates that the subject likes a musical piece while the other state indicates that the subject does not like the musical piece.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

A musical piece may be a song, a composition of vocal and/or instrumental sounds or the like. The musical piece may include a set of features such as pitch or rhythm and when the piece is played, the set of features make up a melody.

In the various embodiments of this invention, a musical piece is played to a subject 108 for his enjoyment. The musical piece may be part of a set of musical pieces. The set of musical pieces may be of different genres or subgenres. However, the artistic nature of a musical piece may mean that the classification (e.g. into genres) of a musical piece may differ based on the person or entity who classifies.

Figure 1:
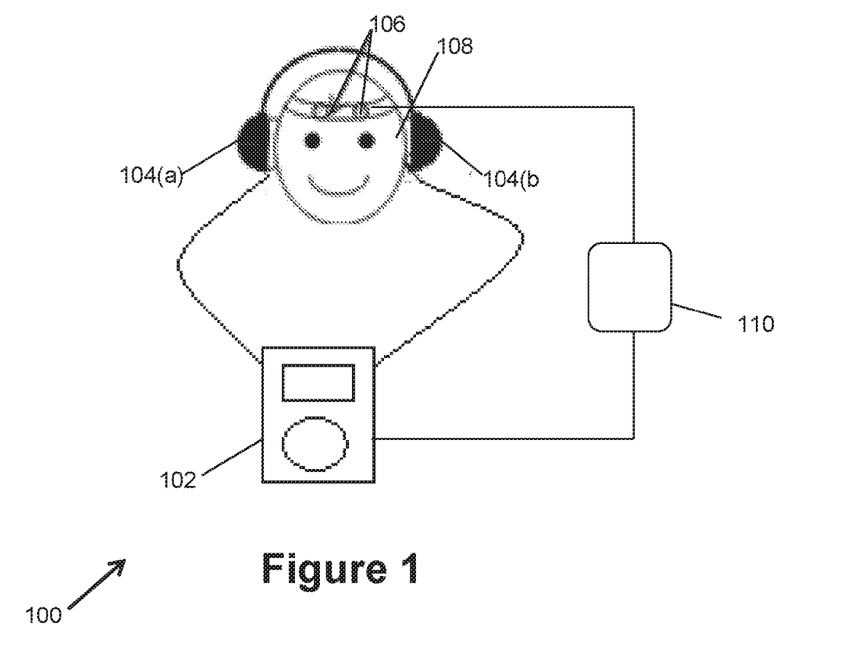
FIG. 1 shows a front planar view of an apparatus in accordance with an embodiment when used by a subject.

Referring to FIG. 1, the set of musical pieces may be played by the subject 108 through a music player 102. The music player 102 may be a MPEG-1 Audio Layer-3 Player (or MP3 Player), CD player or cassette player or any other suitable devices as would be known to a person skilled in the art. Examples of suitable devices are a personal computer, computer tablets or mobile phones. There may be channels 104(a)-(b) which transmit the music pieces to the subject. Examples of channels 104(a)-(b) include earphones and a Bluetooth® headset.

Additionally, at least one electroencephalography ("EEG") electrode 106 may be used to detect the EEG signal of the subject as he listens to the musical pieces. The EEG electrodes are attached at a suitable location of the subject's body (e.g. forehead). Accordingly, the EEG signal will be analyzed to derive features of the EEG signal as the subject listens to at least one of the set of musical pieces. The EEG electrode measures brainwaves that are indicative of the activities of the subject's brain as he listens to the musical piece. In clinical context, the EEG could also refer to the brain's spontaneous electrical activity over a short period of time.

Additionally, software is implemented to analyze and extract musical features associated with each of the set of the musical pieces. The results from the analysis of the EEG signal and the musical pieces may be used to build a training model. This training model may be used for automatically classifying the existing set of musical pieces or a new set of musical pieces. This model may be used to organize the musical pieces in order of the subject's preference or states (e.g., emotional states). The model may also be used to enhance musical parameters of an acoustic signal of the musical pieces in response of the subject's preference.

The software that is implemented is stored onto a device 110. It is to be understood that the analysis of the EEG signal and musical pieces may be done by the same or separate devices. In other words, both the analysis of the EEG signal and musical pieces may be carried out within device 110 or any one of the analysis of the EEG signal and musical pieces may be carried out within device 110. In any case, the EEG signal and the musical pieces will be subject to an analysis process during which the model is built. The same or separate device may use the model for other applications pertaining to the musical pieces.

Figure 2:
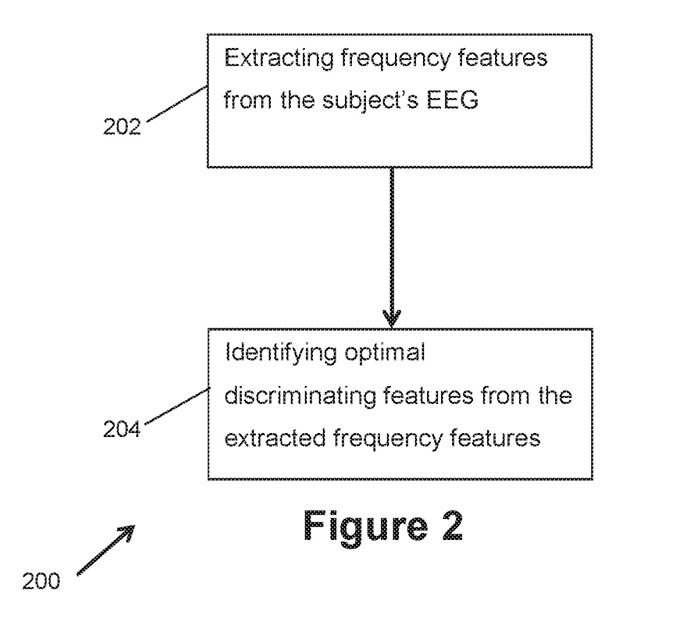
FIG. 2 shows a flowchart that illustrates a method for deriving optimal discriminating features in accordance with the embodiment.

FIG. 2 shows a flowchart 200 that illustrates a method for deriving optimal discriminating features indicative of a subject state when the subject listens to one of a set of musical pieces, in accordance with the embodiment. This method aims to provide an effective way to analyze the EEG signal so as to derive optimal discriminating features. It is to be understood that a computer system may be used to implement the method shown in the flowchart 200. In one embodiment, the computer system may be present in the music player 102 of FIG. 1. In another embodiment, the computer system may be present in the device 110.

In 202, frequency features are extracted from the subject's EEG signal when the subject is in a first subject state and a second subject state. The frequency features includes characteristics of the EEG signal at one frequency band. The step of extracting the frequency features includes extracting the frequency features from more than one frequency band in one set of time segments.

In the embodiment, the EEG signal is decomposed into a plurality of filter bands and time segments. The plurality of filter bands represents the frequency bands from which the frequency features are extracted.

In 204, optimal discriminating features are identified from the extracted frequency features. In the embodiment, the identified optimal discriminating features are those that capture the most discrimination frequency components between the first subject state and the second subject state.

For 202 and 204, one of the first subject state and the second subject state indicates that the subject likes the musical piece while the other state indicates that the subject does not like the musical piece. In the embodiment, the subject indicates via a separate device (e.g. device 110 in FIG. 1) whether he likes the musical piece that he is listening to.

Figure 3:
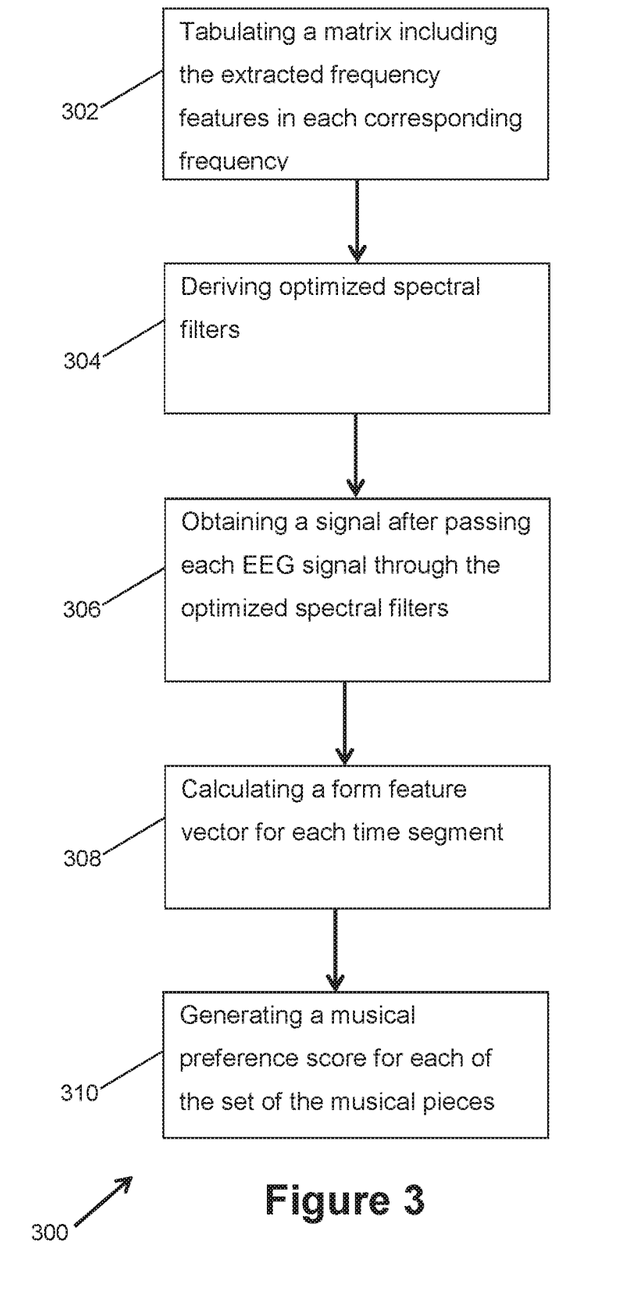
FIGS. 3 and 4 show flowcharts that illustrate methods for using the optimal discriminating features in accordance with the embodiment.

FIG. 3 shows a flowchart 300 that illustrates a method for further steps included in identifying optimal discriminating features in accordance with the embodiment.

In 302, the step of identifying optimal discriminating features includes tabulating a matrix including the extracted frequency features in each corresponding frequency band.

In 304, the step of identifying optimal discriminating features includes deriving optimal spectral filters. Each of the optimal spectral filters is the frequency band associated with the optimal discriminating features. In the embodiment, the optimal spectral filters may maximize the difference in the variance of the EEG signal in the first and second subject state. Additionally or alternatively, the optimal spectral filters may be obtained from the matrix obtained in step 202.

In 306, the step of identifying optimal discriminating features includes obtaining an optimal discriminating signal after passing each EEG signal through the optimal spectral filters. Each EEG signal is obtained when the subject listens to a corresponding one of the set of musical pieces.

In 308, the optimal discriminating signal is used to calculate a form feature vector for each time segment. In the embodiment, the optimal discriminating signal that maximizes the difference in the variance of the EEG signal in the two subject states is associated with the largest eigenvalues associated with the matrix in 302.

In 310, the form feature vector is used to generate a musical preference score for each of the set of the musical pieces. The musical preference score indicates the subject's preference of the musical piece. In the embodiment, the musical preference score may be generated as the subject listens to the musical piece. Alternatively, the musical preference score may be generated after the subject has finished listening to the musical piece.

Figure 4:
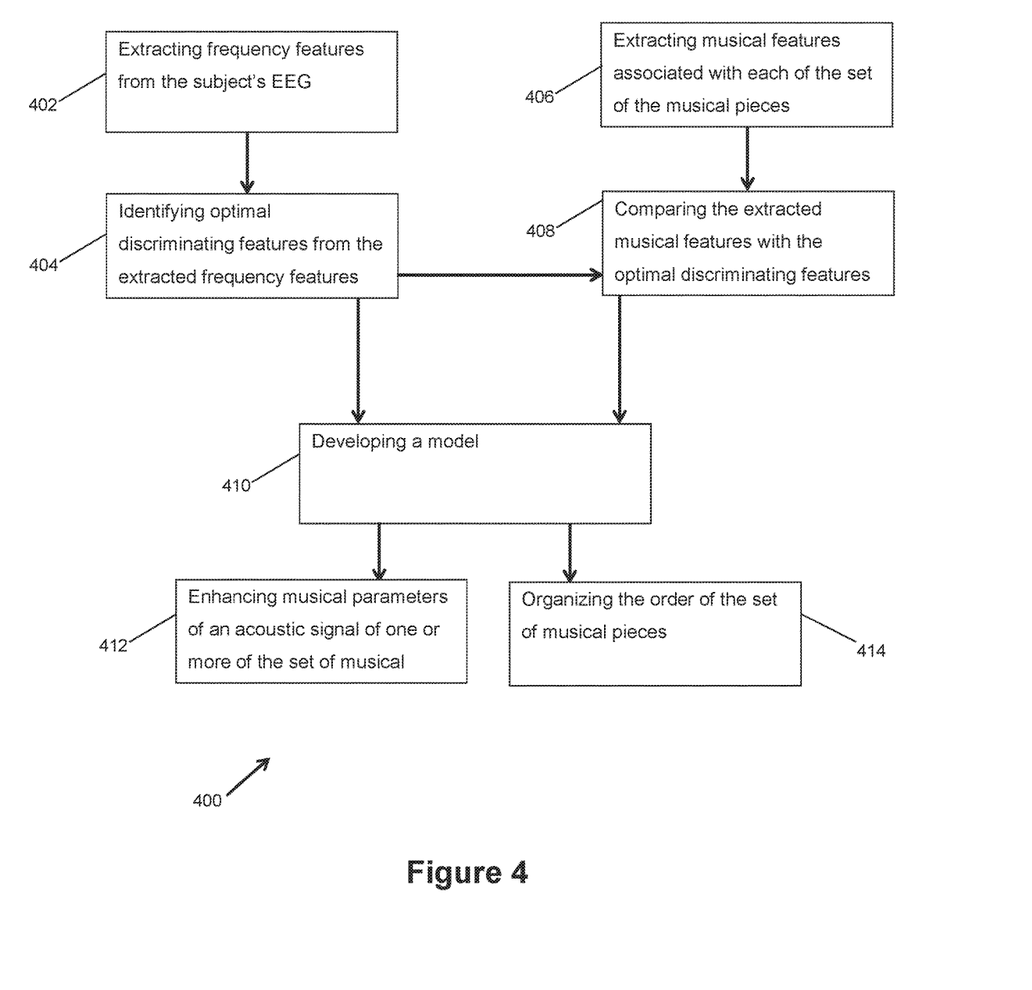

FIG. 4 shows a flowchart 400 that illustrates a method for developing a model indicative of a subject state when the subject listens to one of a set of musical pieces, in accordance with the embodiment. This method aims to provide an effective model that can help detect music preference from an EEG signal and an effective model that finds an association between the EEG signal and the musical pieces.

Operations 402 and 404 may be analogous to operations 202 and 204 of FIG. 2. Accordingly, frequency features are extracted from the subject's EEG signal when listening to one of the list of musical pieces in 402. The step of extracting the frequency features includes extracting the frequency features from more than one frequency band in one set of time segments. Optimal discriminating features are identified from the extracted frequency features in 404. The act of extracting the frequency features extracts the frequency features from more than one frequency band in one set of time segments. The act of identifying optimal discriminating features derives the features indicative of a subject state when the subject listens to one of the set of musical pieces.

It is to be understood that a computer system may be used to implement operations 406, 408, 410, 412 and 414 and may be different from the computer system used to implement operations 402 and 404. In an embodiment, the computer system may be present in the music player. In another embodiment, the computer system may be present in a device separate from the music player.

Figure 8:
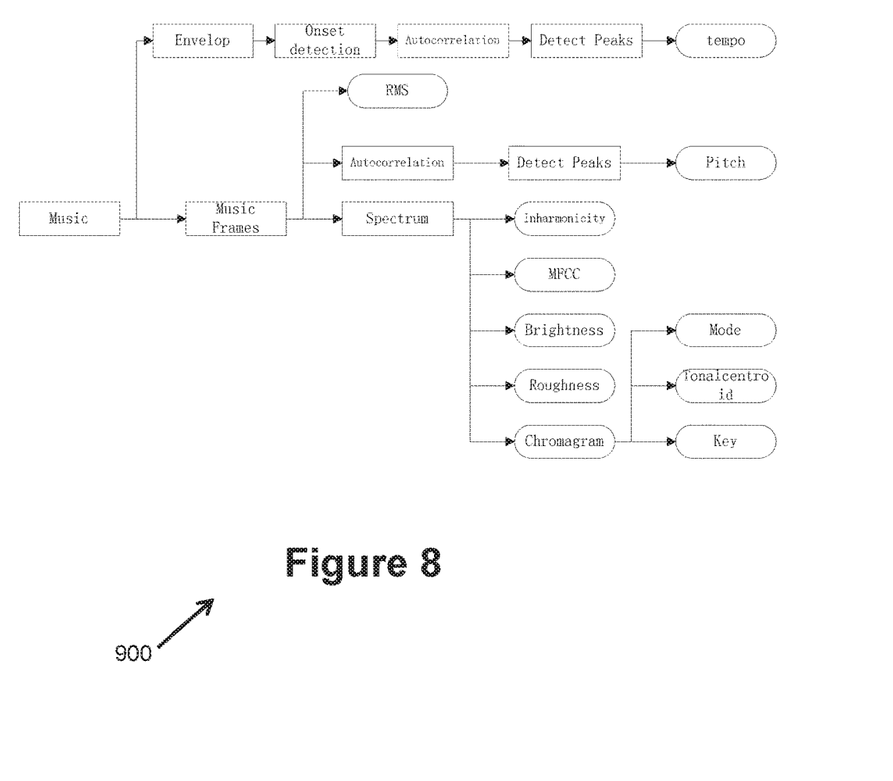
FIG. 8 shows the musical features retrieved by the music feature generation of FIG. 5 in accordance with the embodiment.

In 406, musical features associated with each of the set of the musical pieces are extracted. In the embodiment, the extracted musical features are compared with the optimal discriminating features to determine which of the extracted musical features are indicative of characteristics of musical pieces that the subject prefers. A set of musical features that could be retrieved is shown in FIG. 8 and discussed below.

In 408, the extracted musical features are associated with the optimal discriminating features so as to determine which of the extracted musical features are the most indicative features of musical pieces that affect the subject's preference.

In 410, a model is built, in response to 408. In the embodiment, the model is built using the parameters of the optimal discriminating features identified from the music-evoked EEG signal and of the extracted musical features that are indicative of characteristics of musical pieces that the subject prefers. In one embodiment, the model is used as a training model for the same subject. In an embodiment, the model is trained using at least one further subject and used for at least two subjects who may be the same or different subjects used for operations 412 and 414. In another embodiment, the model is trained using a first plurality of subjects and used for a second plurality of subjects, which may be the same or different from the first plurality of subjects.

In 412, the musical parameters of an acoustic signal of one or more of the set of musical pieces are enhanced in response to the model. In the embodiment, when it is determined that the musical parameters of an acoustic signal are similar to the characteristics that the subject prefers, such musical parameters will be enhanced. For example, if it were determined that the subject prefers musical pieces having bass or singing voices within the lowest range, such musical parameters (e.g., bass or singing voices within the lowest range) will be enhanced or made more prominent.

In 414, the order of the set of musical pieces is organized in response to the model. In accordance with the embodiment, a model organizes the order of the musical pieces based on the parameters used to build the model in operation 410. By way of example, if it were determined that the subject prefers musical pieces having bass or singing voices within the lowest range, musical pieces with musical parameters indicative of such musical features will be ranked higher. The musical pieces that are ranked higher will be placed higher in a new order so as to have a greater positive effect on the subject.

Figure 5:
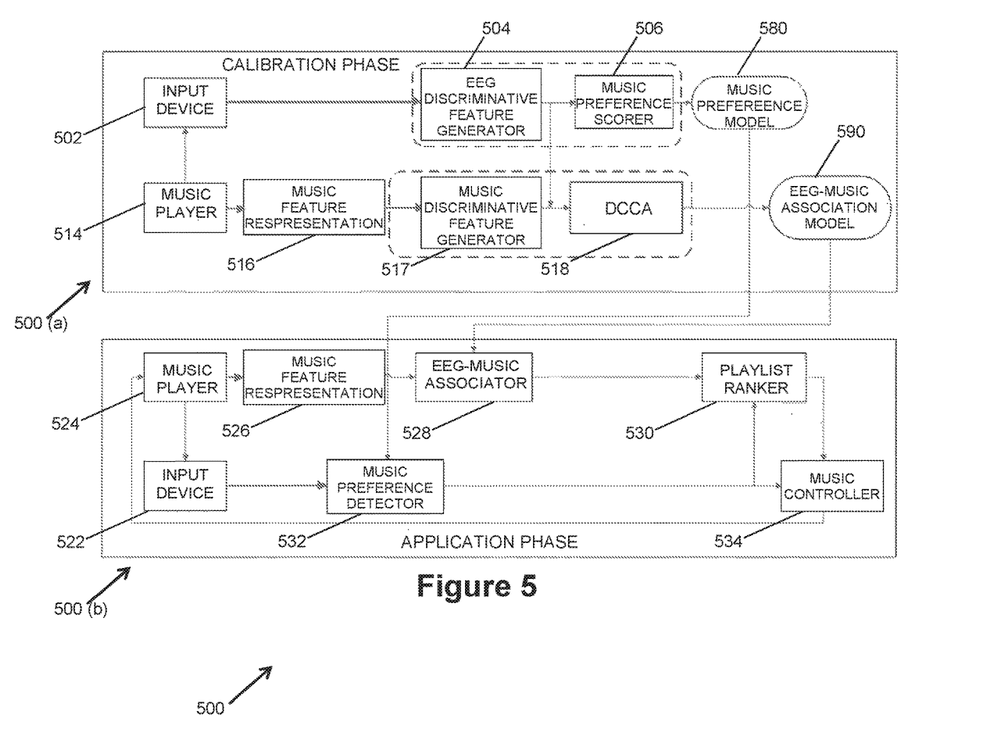
FIG. 5 shows an apparatus in accordance with the embodiment.

FIG. 5 shows an apparatus 500, according to the embodiment. Sensor data is acquired from a subject via an input device 502 (an example is the electrode 106 in FIG. 1) as the subject listens to a musical piece. An example of the input device 502 is a human-machine system or device, for example a subject 108 may listen to music pieces via the music player 102 which may also process the received EEG data and analyze the musical information. In this embodiment, the subject 108 attaches the at least one EEG electrode 106 which is the input device onto the forehead. The at least one EEG electrode 106 may send the EEG data wirelessly to the music player 102.

In the embodiment of calibration phase 500(*a*), the subject indicates his preference of the musical piece after listening to the musical piece by simply selecting "like" or "dislike" (e.g. using mouse to click when 102 is a computer, using touch screen when 102 is a tablet or smart phone).

The input device 502 is operatively coupled to an EEG discriminative feature generator 504. The EEG discriminative feature generator 504 is configured to analyze the EEG signal of the subject in response to the selection of "like" or "dislike". In the embodiment of calibration phase 500(*a*), the EEG signal and the selection would be transmitted to the EEG discriminative feature generator 504 in order to find the most discriminative features of EEG for differentiating two different mental states "like" and "dislike", and the transmitted "selection" is viewed as the true label of the input data EEG for training the model. In the embodiment of online application phase 500(*b*), only the EEG signal would be transmitted to the EEG discriminative feature generator 504, which processes the EEG signal to observe the subject's brain activity to understand whether or not he enjoys or likes the musical piece that is playing.

The EEG signal received from the input device 502 will be decomposed into a plurality of filter banks and a plurality of time segments by the EEG discriminative feature generator 504. In the embodiment, the frequency banks may comprise 13 frequency bands and may cover the delta band to the gamma band (0.5 Hz-48 Hz) with a bandwidth of 4 Hz. The EEG discriminative feature generator 504 may perform filter bank transformation so as to identify the discriminative features that capture the most discriminative features components.

Various embodiments employ the common frequency analysis (CFA) which uses the combination of optimal spectral filter to maximize difference in the variance of the EEG measurements in the first subject state and the second subject state.

In an embodiment, $X_a$ or $X_b$ represents a single channel signal trial EEG for the first subject state and the second subject state. The first subject state indicates that a subject likes or prefers the musical piece and the second subject state indicates that a subject does not like or prefer the musical piece. The method employed by the CFA algorithm is based on the simultaneous diagonalization of two covariance matrices:

$$\Sigma_i = \frac{1}{Q_i} \sum_{Q_i} \frac{X_i X_i^T}{\text{trace}[X_i X_i^T]}, \ i \in \{a, b\} \quad (1)$$

where $\Sigma_i$ are the covariance matrices estimates obtained by the average value of the optimal discriminating signals.

The simultaneous diagonalization can simply be achieved by solving the generalized eigenvalue problem:

$$\Sigma_a W^T = \Lambda \Sigma_b W^T \quad (2)$$

where $\Lambda$ is a diagonal matrix and the largest and smallest diagonal elements in $\Lambda$ are corresponding to the optimized spectral filters which keep most discriminative information.

The signal Z after optimized spectrally filtering of a single trial single channel EEG X is given as:

$$Z = WX \quad (3)$$

The discriminative spectral features are then derived by using variances of only a small number m of the spatial filtered signal Z by the CFA algorithm. The signal $Z_p$, $p \in \{1 \ldots 2m\}$ that maximizes the difference in the variance of the two classes of EEG are associated with the largest eigenvalues $\lambda$ and $1-\lambda$. These signals are used to form feature vector $f_p$ for each time segment. The EEG, discriminative feature vector $f_p$ is then used to compute the music preference score:

$$f_p = \log\left(\text{var}(Z_p) \bigg/ \sum_{i=1}^{2m} \text{var}(Z_p)\right) \quad (4)$$

The EEG discriminative feature generator 504 is coupled to a music preference scorer (or music scorer) 506. In accordance with the embodiment, the music preference scorer 506 uses the generated EEG discriminative features to perform real-time detection of the level of music preference. An example is that the music preference scorer 506 is configured to detect whether the subject likes the musical piece that is currently playing in response to the generated EEG discriminative features.

In accordance with the embodiment, the music preference scorer 506 uses a classification algorithm to model and classify the EEG discriminative musical features in order to obtain the musical preference score based on the probability estimation.

One example of a classification algorithm is a Support Vector Machine (SVM) which maximizes the separation between the two subject states based on the assumption that it improves the classifier's generalization capability.

In accordance with the embodiment, the SVM maximizes the separation between the two classes by minimizing the cost function:

$$J(W) = \frac{1}{2}\|W\|^2 \quad (5)$$

subject to the constraint:

$$Z_i(WX_i - b) \geq 1, \forall i = 1, 2, \ldots, n \quad (6)$$

where $X_i$, $i=1, 2, \ldots, n$ are the training data, b is a bias, and $Z_i \in \{-1, 1\}$ is the label.

The SVM decision function $f(X) = WX - b$ gives the feature space distance of the sample to the hyperplane defined by W, b. It would be understood by a person skilled in the art that the examples lying close to the hyperplane have a larger probability of being misclassified than examples lying further away. In the embodiment, the conditional class probability $p(z|x)$ would be modeled as a function of the value of the SVM decision function:

$$\sigma(f(x_i)) = \frac{1}{1 + e^{-2f(x_i)}} \quad (7)$$

Equation (7) maps the decision function value $f(x_i)$ to the interval [0,1], thus $\sigma$ can be viewed as a probability.

In the embodiment, respective EEG signals of the subject in the first subject state and the second subject state may be collected. The first subject state and the second subject state are denoted as $x_i$, $i=1, 2$. It is assumed that these two states depend on the factor z that can be denoted as two states $z_i$, $i=1$ for 'like' music and $i=2$ for 'dislike' music. The probability of these two states $p(z_1) + p(z_2) = 1$. The class probability of arbitrary x can be respectively denoted by $p(z_1|x)$ for 'like' state and $p(z_2|x)$ for 'dislike' state. The ratio which indicates EEG-based music preference level is:

$$l(x) = \frac{p(z_1 | x)}{p(z_2 | x)} \quad (8)$$

In the embodiment, the outputs of the music preference scorer 506 are the parameters that build the music preference model 580. In the embodiment, the outputs of music preference scorer 506 are tabulated for one set of musical pieces for one subject. In another embodiment, the outputs of music preference scorer 506 are tabulated for one set of musical pieces for at least two subjects.

In the embodiment, the music player 514 could be coupled to a music feature representation 516. The music player 514 is configured to play the musical pieces for training. An example of the music player 514 is the music player 102 in FIG. 1. In the embodiment, a controller (not shown) is coupled to the music player 514 to control the music pieces. The music feature representation 516 could retrieve a set of musical features from an acoustical signal in order to make the further investigation of association between the musical features and music-evoked EEG signal. A set of musical features that could be retrieved is shown in FIG. 8.

In the embodiment, the music feature representation 516 is coupled to a music discriminative feature generator 517. The music discriminative feature generator 517 is configured to perform a correlation analysis for the set of musical features retrieved by music feature representation 516. The analysis is performed to investigate the relationship between musical features and the music preference level in order to perform musical feature selection. The musical feature selection is conducted to compare the extracted musical features with the optimal discriminating features so as to determine which of the extracted musical features are indicative of characteristics of musical pieces that the subject prefers. The set of musical features could be used to predict the music preference level.

In the embodiment, the correlation between each feature type and music preference level is computed to assess the validity of the musical features and select the best predictors. The feature type with the highest correlation could be viewed as the best feature type for predicting music preference level. In addition, stepwise regression between each musical feature and preference level may be computed for the same purpose. This helps to eliminate or reduce the complexity problem with unnecessary redundancy.

In the embodiment, only those musical features whose correlation with ratings to be sufficiently statistically significant (with p-value lower than 0.05) are selected. The selected features are ordered from the most correlated to the least correlated. In the embodiment, features that are not sufficiently independent with respect to the better scoring features (with a normalized cross-correlation exceeding 0.6) are deleted.

In the embodiment, the music discriminative feature generator 517 and the EEG discriminative feature generator 504 may be coupled to a Discriminative Canonical Correlation Analyzer (DCCA) 518. The DCCA 518 is configured to find out the association between music acoustic signal and music evoked EEG signal. The generated EEG discriminative features from the EEG discriminative feature generator 504 and the musical features from the music feature representation 516 could be correlated to obtain a new feature that highlights the most important features reflecting music properties.

In the embodiment, a discriminative CCA (DCCA) 518 that maximizes the correlation of the two groups and the discrimination of two classes at the same time is utilized to improve the music preference scoring performance. The DCCA 518 may be a supervised CCA.

In an embodiment, there could be a set of pair-wised samples $\{(x_i, y_i)\}_{i=1}^n \in R^p \times R^q$, where $x_i$ and $y_i$ are optimized features obtained from a music-evoked EEG and from the music itself. The pair-wised samples $\{(x_i, y_i)\}_{i=1}^n$ could belong to two subject states: like and dislike. Suppose that $X=[x_1, \ldots x_n] \in R^{p \times n}$ and $Y=[y_1, \ldots y_n] \in R^{q \times n}$, where p and q are the dimension of feature vector for the EEG and the music respectively, and X, Y are centralized. One advantage of DCCA is to find two sets of basis vectors $\omega_x \in R^p$ and $\omega_y \in R^q$ for X and Y, so that the correlation coefficients between $\omega_x X$ and $\omega_y Y$ are maximized. At the same time, the discrimination between projected data of different classes are maximized. The optimization problem can be formulated as following:

$$\rho = \max_{\omega_x, \omega_y} \frac{\omega_x^T (C_w - C_b) \omega_y^T}{\sqrt{(\omega_x^T C_{xx} \omega_x)(\omega_y^T C_{yy} \omega_y)}} \quad (9)$$

Where:

$$C_w = \sum_{j,k \in \text{same class}} (x_j y_k^T + x_k y_j^T) \quad (10)$$

$$C_b = \sum_{j,k \in \text{different classes}} (x_j y_k^T + x_k y_j^T), \quad$$

$$C_{xx} = XX^T, \quad (11)$$

$$C_{yy} = YY^T \quad (12)$$

$C_w$ denotes the correlations of $x_i, y_i$ from the same classes, $C_b$ denotes the correlations of $x_i, y_i$ from the different classes.

The solution for equation (9) can be obtained by computing a generalized eigenvalue problem:

$$(C_w - C_b)(YY^T)^{-1}(C_w - C_b)^T w_x = \lambda^2 XX^T w_x$$

$$(C_w - C_b)(XX^T)^{-1}(C_w - C_b)^T w_y = \lambda^2 YY^T w_y \quad (13)$$

After obtaining eigenvectors $W_x$ and $W_y$ corresponding to the largest d generalized eigenvalues $\lambda_i$, i=1 . . . d, features for X and Y, can be extracted by the following equations:

$$\tilde{X} = W_x^T X, \quad (14)$$

$$\tilde{Y} = W_y^T Y \quad (15)$$

It is possible to use $\tilde{X}$ and $\tilde{Y}$ separately or use them by combining them as $$\tilde{X} + \tilde{Y} \text{ or } \begin{pmatrix} \tilde{X} \\ \tilde{Y} \end{pmatrix},$$

or simply use $\tilde{X}$ or $\tilde{Y}$. In the embodiment, EEG-Music associated music feature can be obtained from Equation (14). In the embodiment, the outputs of the DCCA 518 are the parameters that build the EEG-music association model 590.

In the embodiment, the above description for FIG. 5 relates to a calibration phase 500(*a*). The calibration phase 500(*a*) could be carried out with one subject to train a subject specific model. Additionally or alternatively, the calibration phase 500(*a*) could be carried out with one further subject to train a general model. In another embodiment, the calibration phase 500(*a*) is carried out with a plurality of subjects.

In an embodiment, the parameters that build the music preference model 580 are transmitted to a music preference detector 532 in an application phase. During an application phase, a music player 524 (analogous to music player 514) plays a set of musical pieces to a subject via an input device 522. An example of the music player 524 is the music player 102 in FIG. 1. The set of musical pieces that are played during the application phase may be the same or different from the set of musical pieces played during the calibration phase 500(*a*). Similarly, the subject in the application phase 500(*b*) may be the same or different from the subject in the calibration phase 500(*a*).

The input device 522 is analogous to the input device 502 in the calibration phase. Sensor data is acquired from a subject in a system via the input device 522, as the subject listens to a musical piece. An example of the system is shown in FIG. 1 and includes the music player 102, the channels 104, the electrode 106 and the subject 108.

In an embodiment, the input device 522 is operatively coupled to the music preference detector 532. The music preference detector 532 receives the parameters from the music preference scorer 580 and uses these parameters to determine an indicator of the music preference level based on the evoked EEG signals. In the embodiment, it is determined that a subject likes a musical piece if $p(z_1|x) > p(z_2|x)$. The indicator is a music preference score and is determined using the parameters from the music preference scorer 580.

In the embodiment, the music preference detector 532 is operatively coupled to an online music playback controller (or music controller) 534. The online music playback controller 534 could organize the order of the set of musical pieces by the musical preference score that is associated with the musical piece. By way of example, a musical piece that is associated with a higher musical preference score than another musical piece would be placed higher in the order of the set of musical pieces.

The online music playback controller 534 is configured to receive the ratio tabulated in equation (8) and provide a music preference class information based on the criterion below:

$$\begin{cases} l(x) > 1 + \delta, & x \in \text{'like' class} \\ l(x) \in [1 - \delta, 1 + \delta], & x \in \text{'neutral' class} \\ l(x) < 1 - \delta, & x \in \text{'dislike' class} \end{cases}$$

where $\delta$ is a constant to be empirically set. In the embodiment, the EEG signal is tabulated at a regular interval (e.g., 25 s).

The music preference class information is used to control the musical pieces that would be played in response to the music preference class information provided in online music playback controller 534. When the music preference class information indicates that the subject likes the musical piece that is being played ($l(x)>1+\delta$), the controller 534 is configured to control the musical piece such that it will continue to play. When the music preference class information indicates that the subject does not like the musical piece that is being played ($l(x)>1+\delta$), the controller is configured to control the musical piece such that it will skip to the next musical piece. In an embodiment, when the music preference class information indicates that the subject is neutral towards the musical piece that is being played ($l(x)\in[1-\delta, 1+\delta]$), the controller is configured not to take any action.

In the embodiment, the playlist ranker 530 is configured to receive the music preference score and the music feature from the EEG-music associator 528 to rank the music database and rank the order of the set of the musical pieces.

In the embodiment, the dissimilarity of two musical pieces is measured through a distance metric. An example is Mahalanobis distance:

$$d(y_1,y_2) = \sqrt{(y_1-y_2)^T S^{-1} (y_1-y_2)} \quad (16)$$

where S is a covariance matrix.

The similarity of two pieces of music can be represented by:

$$s(y_1, y_2) = \frac{1}{d(y_1, y_2)} \quad (17)$$

In the event that the music preference score indicates that the subject likes the current musical piece, the current mode will be identified as 'like'. Further, the database of musical pieces will be ranked based on the similarity of each musical piece in the database to the musical piece that is playing. The set of musical pieces will be reorganized based on the descending order of the ranking.

In the event that the music preference score indicates that the subject dislikes the current musical piece, the current mode will be identified as 'dislike'. Further, it is assumed that musical pieces that are similar to the current musical piece would also be "disliked" by the subject.

The music playlist updating rule for the case is updated for the subject "dislikes" the current musical piece given the music preference score l(x) and a predefined minimum moving order $N_{min}$ and minimum similarity $s_{min}$. The current musical piece y and its neighborhood with music $s(y_i,y) > s_{min}$ to order $N_{min}/l(x)$ of the music playlist may be moved.

In the embodiment, the online music playback controller 534 is operatively coupled to the music player 524. In the embodiment, the online music playback controller 534 controls the order on how the set of musical pieces would be played via a controller (not shown). The music player 524 would play the set of musical pieces in the order determined by the online music playback controller 534.

In the embodiment, the music player 524 is operatively coupled to a music feature representation 526 which is analogous to music feature representation 516. The music feature representation 516 could retrieve a set of musical features from the acoustical signal in order to make the further investigation of association between the musical features and music-evoked EEG signal. A set of musical features that could be retrieved is shown in FIG. 8. In the embodiment, the music feature representation 526 is further configured to calculate the form feature vector.

In the embodiment, the music preference detector 532 is operatively coupled to a playlist ranker 530. In the embodiment, the playlist ranker 530 could also rank the set of musical pieces that the subject is listening to by the musical preference score that is associated with the musical piece.

In the embodiment the music feature representation 526 is operatively coupled to an EEG-music associator (or model builder) 528. In the embodiment, the parameters for a EEG-music association model 590 are sent to the EEG-music associator 528. The trained EEG-music association model 590 is then used in the EEG-music associator 528 to give high weight to the musical features that are highly correlated to the subject's preference and give low weight to or even discard the musical features that are weakly correlated to the subject's preference.

In the embodiment, the EEG-music associator 528 is operatively coupled to the playlist ranker 530. The results of the weighted music features will be used by the playlist ranker 530 to rank the set of musical pieces that the subject is listening to.

Figure 6:
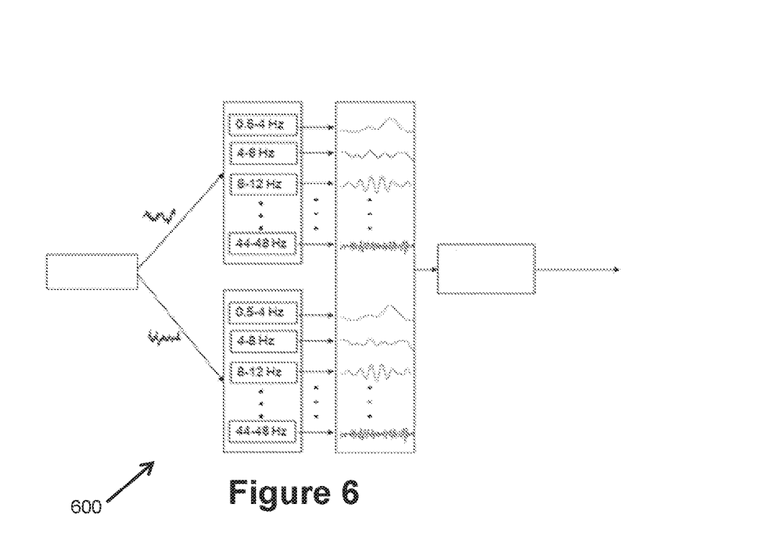
FIG. 6 shows a diagram depicting how the EEG signal is decomposed in accordance with the embodiment.

FIG. 6 shows how the EEG signal is decomposed into filter banks by the EEG discriminative feature generator 504 in accordance with the embodiment.

Figure 7:
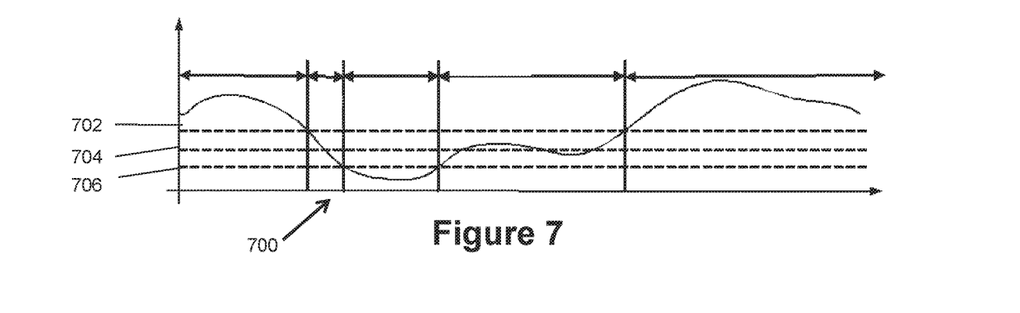
FIG. 7 shows a graph depicting how the online music playback controller of FIG. 5 may be configured to control the set of musical pieces in accordance with the embodiment.

FIG. 7 shows how the online music playback controller 534 is configured to control the set of musical pieces. Lines 702 and 704 represent the musical preference class information to be 1+δ and 1, respectively. In other words, lines 702 and 704 represent "like" and "neutral" state for the music preference class information. When it is determined that the music preference state information is like and neutral, the musical piece that is playing will continue to play. Line 706 represents the musical preference class information to be 1−δ. This means that line 706 represents that the subject dislikes the musical piece that is currently playing. When it is determined that the musical preference state information is "dislike", the musical piece that is currently playing will stop and the music player will skip to the next musical piece. In the embodiment, the playlist ranker 530 may be coupled to the online music playback controller 534.

FIG. 8 shows the features 900 that are held for consideration and the steps to derive these features. In an embodiment, the features are extracted by music feature representation 516 or 526. The retrieved musical features include but are not limited to:

1. Root-mean-square (RMS): root average of the square of the amplitude
2. Tempo: estimated by detecting periodicities from the onset detection curve
3. Brightness: estimated by measuring the amount of energy above a cut-off frequency.
4. Roughness: estimated depending on the frequency ratio of each pair of sinusoids. An estimation of the total roughness is computed by computing the peaks of the spectrum, and taking the average of all the dissonance between all possible pairs of peaks
5. Mel-frequency cepstral coefficients (MFCC): MFCC is a representation of the short-term power spectrum of a sound based on a linear cosine transform of a log power spectrum on a nonlinear mel scale of frequency. MFCC offers a description of the spectral shape of the sound
6. Pitch: is estimated by computing an autocorrelation and then a peak picking is applied to the autocorrelation function.
7. Inharmonicity: estimates the inharmocicity, i.e., the amount of partials that are not multiples of the fundamental frequency, as a value between 0 and 1. More precisely, the inharmonicity considered here takes into account the amount of energy outside the ideal harmonic series.
8. Key: a broad estimation of tonal center positions and their respective clarity.
9. Chromagram: also called harmonic pitch class profile, which shows the distribution of energy along the pitches or pitch classes.
10. Mode: estimates the modality, i.e. major vs. minor
11. Tonalcentroid: a 6-dimensional tonal centroid vector corresponds to a projection of the chords along circles of fifths, of minor thirds, and of major thirds.
12. Entropy: it is the relative Shannon entropy of the music segment.

Figure 9:
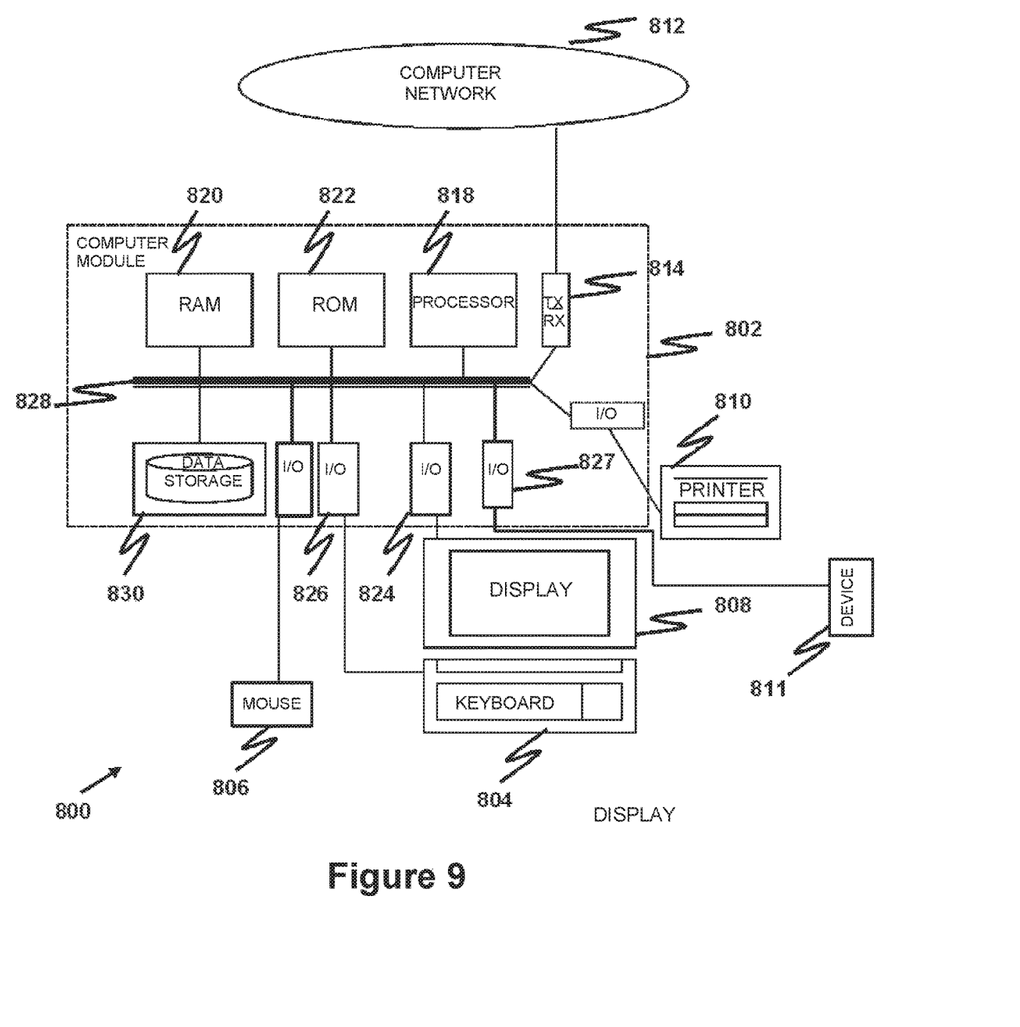
FIG. 9 shows a computer system for performing a method for deriving optimal discriminating features in accordance with an embodiment.

FIG. 9 shows an exemplary computer system 800 for use in performing the abovementioned operations, for example, as part of a music feature generation. In the embodiment, the computer system performs operations 202 to 204 of FIG. 2, operations 302 to 310 of FIG. 3 and operations 402 to 414 of FIG. 4. In the embodiment, the computer system 800 is part of the music player 102 which may be a smartphone or a tablet.

The computer system 800 includes a computer module 802, input modules such as a keyboard 804 and mouse 806 and a plurality of output devices such as a display 808, printer 810 and a device 811.

The computer module 802 is connected to a computer network 812 via a suitable transceiver device 814, to enable access to, for example, the Internet or other network systems, such as, a Local Area Network (LAN) or a Wide Area Network (WAN).

The computer module 802 in the example includes a processor 818, a Random Access Memory (RAM) 820 and a Read Only Memory (ROM) 822. The computer module 802 also includes a number of Input/Output (I/O) interfaces, for example I/O interface 824 to the display 808, interface 826 to the keyboard 804 and I/O interface 827 to the device 811.

The components of the computer module 802 typically communicate via an interconnected bus 828 and in a manner known to the person skilled in the relevant art.

The computer system 800 may function in accordance with software stored on the RAM 820 and/or the ROM 822. The software may include an operating system and one or more application programs. An application program may be supplied to the user of the computer system 800 encoded on a data storage medium, such as, a CD-ROM or flash memory carrier and read utilizing a corresponding data storage medium drive of a data storage device 830. The application program may be read and controlled in its execution by the processor 818. Intermediate storage of program data may be accomplished using RAM 820.

It is to be understood that the computer system 800 provides a non-limiting example of a suitable computer system. In some embodiments, one or more elements may be combined together into the same element. In some embodiments, one or more elements may be absent or duplicated. Additional elements may be present in some embodiments.

Experiments and Discussion

Data Collection

EEG signals were acquired using a NeuroSky-MindBand with a sampling rate of 256 Hz. For the purposes of the experiments, two EEG electrodes were attached horizontally onto the subjects' foreheads. The left and right electrodes corresponded to FP1 and FP2 (106, FIG. 1), respectively.

The data was collected from twenty-one healthy subjects. Each subject was instructed to sit comfortably and keep body movements to a minimum while they listened to music. The subjects were also instructed to keep their eyes open. Additionally, the subject was given some time to calm down prior to listening to the music so that they may concentrate on the music.

Two sessions were conducted on two different days for each subject. Each session was made up of three runs in about an hour. All the subjects were advised to take a little break after each run in each session. At the beginning of each session, the subject was asked to choose four genres from ten available genres (Alternative Rock, Classic, Electro, Heavy Metal, Hip Hop, Jazz Blues, Oldies, Pop, Reggae, and Rock). Three sets of musical pieces were generated from random selections of musical pieces from the music database for the four chosen genres. Each set of musical pieces included twenty pieces of music, each musical piece having a length about thirty seconds each. Each set of musical pieces was played in one run, during which the subject would listen to the music continuously and label each piece of music after the musical piece ended. The subjects would also indicate whether they like, dislike or feel neutral about each musical piece to obtain the true labels for the experiment. A total of 120 EEG signals were obtained for each subject. Consequently, a "5 times 5-fold" cross-validation was performed on each subject's data so as to evaluate the performance.

Music Preference Classification Based on EEG Discriminative Feature Generation

Experiments were carried to compare the conventional methods and embodiments of this invention. Table 1 shows the classification results of several combinations of feature extraction methods and classifiers that are conventionally known. The same frequency band was used for the EEG signal at 0.5-48 Hz. The test accuracies were obtained by "5 times 5-fold" cross validation for each subject. The results shown in Table 1 are the average values and standard deviations across the twenty-one subjects. It can be seen that embodiments of this invention obtained the highest accuracy as compared to other methods. The conventional methods used are principal component analysis (PCA), spectral filter, differential asymmetry of twelve electrode pairs (DASM), logistic regression and binary Fisher discriminant analysis (BFDA).

TABLE 1

Average accuracy of different feature extraction methods and classifiers

| Classifier | BFDA | Logistic-regression | SVM |
|---|---|---|---|
| CFP | 67.23 ± 7.83 | 69.41 ± 8.37 | 75.41 ± 5.13 |
| PCA | 59.28 ± 9.81 | 58.52 ± 10.18 | 66.69 ± 7.03 |
| Spectral Filter | 61.51 ± 10.34 | 63.11 ± 8.96 | 71.68 ± 6.04 |
| DASM | 64.89 ± 7.56 | 62.39 ± 7.27 | 69.38 ± 6.58 |

Music Preference Classification: General Model

In the previous section, the results based on the subject specific model in accordance with an embodiment are shown. A subject specific model is a training model used on one subject which is built using the data of the same subject.

Besides the subject specific model mentioned in the previous section, data from nine random subjects out of the twenty-one subjects were taken to provide a general training model which is then implemented on the other twelve subjects.

A comparison between a general training model and a subject specific model is made, as shown in Table 2.

TABLE 2

Accuracy of a general model case compared with a subject specific model

| | General model | Subject specific model |
|---|---|---|
| 1 | 69.81 | 81.13 |
| 2 | 75.00 | 71.07 |
| 3 | 72.72 | 81.45 |
| 4 | 68.88 | 68.89 |
| 5 | 65.95 | 75.74 |
| 6 | 74.46 | 51.91 |
| 7 | 67.34 | 60 |
| 8 | 66.67 | 68.75 |
| 9 | 66.67 | 70.95 |
| 10 | 70.49 | 69.83 |
| 11 | 64.70 | 80.39 |
| 12 | 74.51 | 67.05 |
| Mean | 69.77 | 70.60 |

Music Feature Generation and EEG-Music Association

The music discriminative feature generation was evaluated by comparing the classification results of music preferences using a full feature set to the results of those using selected features by mutual information or based on correlations as described above. The EEG and music signal association were evaluated by comparing the music preference classification results of the three methods (full feature, mutual information, correlation) purely based on music information to the other two methods (CCA, DCCA) associating music with EEG information and extracting the music information based on the music-EEG association. The results for twenty-one independent experiments are shown in Table 3.

TABLE 3

Classification Accuracy of Music Preference using Different Music Feature Generation Method

| Subject | full music features | Mutual Information | correlation | CCA | DCCA |
|---|---|---|---|---|---|
| 1 | 63.77 | 73.58 | 79.25 | 75.85 | 78.12 |
| 2 | 58.11 | 64.53 | 67.17 | 67.92 | 69.96 |
| 3 | 61.07 | 68.57 | 72.50 | 68.21 | 70.26 |
| 4 | 85.78 | 85.78 | 84.89 | 66.22 | 88.35 |
| 5 | 76.21 | 76.21 | 77.24 | 64.83 | 81.33 |
| 6 | 52.69 | 52.69 | 66.92 | 57.69 | 69.33 |
| 7 | 56.30 | 64.44 | 71.11 | 70.37 | 74.01 |
| 8 | 80.00 | 86.81 | 85.11 | 80.85 | 88.10 |
| 9 | 83.85 | 87.69 | 88.08 | 89.23 | 91.91 |
| 10 | 86.79 | 86.79 | 85.00 | 75.36 | 89.39 |
| 11 | 85.82 | 88.00 | 88.73 | 86.91 | 92.14 |
| 12 | 60.43 | 63.83 | 74.47 | 73.62 | 80.21 |
| 13 | 60.00 | 61.78 | 75.56 | 68.00 | 81.94 |
| 14 | 67.23 | 70.21 | 77.02 | 74.89 | 80.65 |
| 15 | 73.62 | 74.04 | 74.47 | 73.62 | 80.21 |
| 16 | 61.22 | 61.22 | 73.88 | 73.06 | 77.36 |
| 17 | 64.00 | 75.20 | 78.80 | 78.40 | 80.75 |
| 18 | 64.38 | 66.88 | 81.25 | 73.13 | 75.32 |
| 19 | 63.33 | 64.58 | 69.17 | 65.83 | 75.10 |
| 20 | 61.96 | 67.45 | 72.16 | 68.24 | 70.28 |
| 21 | 72.88 | 74.92 | 77.29 | 69.49 | 78.21 |
| Average | 68.54 | 72.15 | 77.14 | 72.46 | 79.66 |

Conventional Methods for Music Preference Classification

PCA

In principal components analysis (PCA) a reduced set of m components or factors that account for most of the variance are extracted from a set of p variables or factors that accounts for most of the variance in the p variables. In other words, it is an objective to reduce a set of p variables to a set of m underlying superordinate dimensions.

Spectral Filter

Spectral filter utilises Fourier analysis, a commonly used transformation, to look at specific frequency bands of signals recorded from each electrode. In the experiment, the frequency range for the Fourier transform is 0.5-48 Hz. Short-time Fourier transform (STFT) with Hanning window of time interval and with a 50% overlap is used to extract the power spectral density value over time. Spectral powers of EEG components are typically adopted where EEG components are defined according, to frequency range, including delta (0.5-3 Hz), theta (4-7 Hz), alpha (8-13 Hz), beta (14-30 Hz) and gamma (31-48 Hz). Therefore, after applying STFT, a power value of each EEG components across time over each channel is derived.

DASM

DASM is the abbreviation for differential asymmetry of 12 electrode pairs and is conventionally known. It is possible to derive the DASM12 after obtaining the spectral powers, which is a power difference at each symmetric electrode pair. For the purposes of the experiment, the power difference between the two electrodes was obtained.

Logistic Regression

Logistic regression is a type of regression analysis used for predicting the outcome of dependent variables which may take on one of a limited and usually fixed number of possible values. This means that logistic regression is typically used in estimating empirical values of the parameters in a qualititative response model (involving one or more discrete random variables whose conditional probability distribution given the values of variables is specified up to a finite number of unknown parameters). Logistic regression is also typically known to be used when there are only two categories of the dependent variables because it measures the relationship between a dependent variable and one or more independent variables, which are usually (but not necessarily) continuous by using probability scores as the predicted values of the dependent variable.

BFDA Binary Fisher Discriminant Analysis

FDA aims to find a linear projection of the data such that the ratio of between group variability to within group variability is maximized in order to classify different classes. BFDA is a specific form of FDA that is used to classify two classes.

It is known to identify features of a musical piece so as to categorize similar musical pieces together based on a subject's manual selection to indicate preference. However, this still requires consideration of the musical features of the musical pieces. Analysis of musical pieces based on their musical features is typically incorrect and the conventional methods do not provide an effective means to accurately categorize the musical pieces in response to a subject's preference. However, an advantage of the above-described embodiments is that brain activity of the subject is detected and analyzed to provide a training model which associates such EEG signal and musical features of the subject's preferred musical pieces.

It is an advantage of the above-described embodiments that the CFA is used to identify the optimal discriminating features. It is a further advantage that an association model associating the EEG signal and the musical features of the musical pieces is generated. This is advantageous because, as shown above, the CFA can identify the optimal discriminating features of an EEG signal and thereby help to provide a musical preference score, and the association model can enhance musical features of an acoustic signal, which can be used to generate a new order of a list of musical pieces in descending order of a subject's preference level.

While several exemplary embodiments have been presented in the foregoing detailed description of the invention, it should be appreciated that a vast number of variations exist, including variations as to how the outputs of the EEG discriminative feature generator 504 may be used to give a preference score for the musical piece. In one embodiment, the output of the EEG discriminative feature generator may be used to estimate the asynchronous music preference probability so as to give a preference score.

It is to be understood that one or more features from one of the above-described embodiments may be combined with one or more features from one or more other above-described embodiments to form different embodiments which fall within the scope of the appended claims.

It will be appreciated by a person skilled in the art that numerous variations and/or modifications may be made to the present invention as shown in the specific embodiments without departing from the scope of the appended claims as broadly described. The present embodiments are, therefore, to be considered in all respects to be illustrative and not restrictive.

What is claimed is:

1. A method for deriving optimal discriminating features indicative of a subject state when the subject listens to one of a set of musical pieces, the method comprising:
    extracting frequency features from the subject's EEG signal when the subject is in a first subject state and a second subject state, the frequency features being extracted from more than one frequency band in one set of time segments;
    identifying optimal discriminating features from the extracted frequency features, the optimal discriminating features indicative of characteristics of the EEG signal when the subject is in the first subject state and the second subject state;
    extracting musical features associated with each of the set of the musical pieces; and
    comparing the extracted musical features with the optimal discriminating features to determine which of the extracted musical features are indicative of characteristics of musical pieces that the subject prefers,
    wherein one of the first subject state and the second subject state indicates that the subject prefers a musical piece while the other state indicates that the subject does not prefer the musical piece.

2. The method according to claim 1, wherein the step of identifying optimal discriminating features includes tabulating a matrix including the extracted frequency features in each corresponding frequency band.

3. The method according to claim 1, wherein the step of identifying optimal discriminating features includes deriving optimal spectral filters, each of the optimized spectral filters being frequency band associated with the optimal discriminating features.

4. The method according to claim 3, wherein the step of identifying optimal discriminating features includes obtaining a signal after passing each EEG signal through the optimal spectral filters, each EEG signal being obtained when the subject listens to a corresponding one of the set of musical pieces.

5. The method according to claim 4, wherein the signal is used to calculate a form feature vector for each time segment.

6. The method according to claim 5, wherein the form feature vector is used to generate a musical preference score for each of the set of the musical pieces, the musical preference score indicating the subject's preference of the musical piece.

7. The method according to claim 6, wherein the musical preference score is used to control the set of the musical pieces, wherein the musical pieces is controlled to stop playing when the musical preference score indicates that the subject does not prefer the musical piece.

8. The method according to claim 1 further comprising developing a model in response to the optimal discriminating features of the subject when listening to one of the set of the musical pieces and the musical features for the one of the set of the musical pieces.

9. The method according to claim 8, wherein the model is used for enhancing musical parameters of an acoustic signal of one or more of the set of musical pieces.

10. The method according to claim 8, wherein the model is used to organize the order of the set of musical pieces.

11. The method according to claim 8, wherein the set of musical pieces are stored in an external database.

12. The method according to claim 8, wherein the step of developing the model further comprises developing the model in response to the optimal discriminating features of one or more other subjects when listening to the one of the set of the musical pieces and the musical features for the one of the set of the musical pieces.

13. A method for developing a model indicative of a subject state when the subject listens to one of a set of musical pieces, the method comprising:
    extracting frequency features from the subject's EEG signal when the subject is in a first subject state and a second subject state, the frequency features being extracted from more than one frequency band in one set of time frames;

identifying optimal discriminating features from the extracted frequency features, the optimal discriminating features indicative of similar characteristics of the EEG signal when subject is in the first subject state and the second subject state;

extracting musical features associated with each of a set of the musical pieces;

comparing the extracted musical features with the optimal discriminating features to determine which of the extracted musical features are indicative of characteristics of musical pieces that the subject prefers; and developing a model in response to the optimal discriminating features of the subject when listening to one of the set of the musical pieces and the musical features for the one of the set of the musical pieces, wherein one of the first subject state and the second subject state indicates that the subject likes a musical piece while the other state indicates that the subject does not like the musical piece.

14. The method according to claim 13, wherein the step of developing the model further comprises developing the model in response to the optimal discriminating features of one or more other subjects when listening to the one of the set of the musical pieces and the musical features for the one of the set of the musical pieces.

15. The method according to claim 13, wherein the model is used for enhancing musical parameters of acoustic signal of one or more of the set of musical pieces.

16. The method according to claim 13, wherein the model is used to organize the order of the set of musical pieces.

17. The method according to claim 13, wherein the EEG signal is obtained by at least one electrode, the at least one electrode being placed on the forehead of the subject.

18. A system for developing a model indicative of a subject state when the subject listens to one of a set of musical pieces, comprising:

an input device for the system operable to receive electroencephalography (EEG) signal;

an EEG discriminative feature generator operable to extract frequency features from the received EEG signal when the subject is in a first subject state and a second subject state and identify optimal discriminating features from the extracted frequency features, the optimal discriminating features indicative of similar characteristics of the EEG signal when subject is in the first subject state and the second subject state;

a model builder operable to develop a model in response to the optimal discriminating features of the subject when listening to one of the set of the musical pieces and the musical features for the one of the set of the musical pieces;

a music scorer operable to extract musical features associated with each of the set of the musical pieces, compare the extracted musical features with the optimal discriminating features from the extracted frequency features to determine which of the extracted musical features are indicative of characteristics of musical pieces that the subject prefers, and generate a musical preference score for each of the set of the musical pieces in response to the extracted musical features associated with that one of the set of the musical pieces, the musical preference score indicating the subject's preference of the musical piece; and a music controller operable to control the set of the musical pieces, wherein the musical pieces is controlled to stop playing when the musical preference score indicates that the subject does not prefer the musical piece, wherein one of the first subject state and the second subject state indicates that the subject prefers a musical piece while the other state indicates that the subject does not prefer the musical piece.

* * * * *

UNITED STATES PATENT AND TRADEMARK OFFICE
CERTIFICATE OF CORRECTION

PATENT NO. : 9,557,957 B2
APPLICATION NO. : 14/428852
DATED : January 31, 2017
INVENTOR(S) : Guan et al.

It is certified that error appears in the above-identified patent and that said Letters Patent is hereby corrected as shown below:

On the Title Page

Item (71), in "Applicant", in Column 1, Line 1, delete "Technology," and insert --Technology-- therefor Signed and Sealed this
Tenth Day of April, 2018

Andrei Iancu
*Director of the United States Patent and Trademark Office*